(12) United States Patent
Elgort et al.

(10) Patent No.: US 10,346,480 B2
(45) Date of Patent: Jul. 9, 2019

(54) SYSTEMS, APPARATUS, AND METHODS FOR SOCIAL GRAPH BASED RECOMMENDATION

(71) Applicants: SONY CORPORATION, Tokyo (JP); SONY CORPORATION OF AMERICA, New York, NY (US)

(72) Inventors: Vladimir Elgort, Staten Island, NY (US); Nobuo Tanaka, Glen Rock, NJ (US); Kentaro Nakamura, Kanagawa (JP); Loren McRoss, San Jose, CA (US)

(73) Assignees: SONY CORPORATION OF AMERICA, New York, NY (US); SONY CORPORATION, Tokyo (JP)

( * ) Notice: Subject to any disclaimer, the term of this patent is extended or adjusted under 35 U.S.C. 154(b) by 385 days.

(21) Appl. No.: 14/853,754

(22) Filed: Sep. 14, 2015

(65) Prior Publication Data

US 2016/0004788 A1     Jan. 7, 2016

Related U.S. Application Data

(63) Continuation of application No. PCT/US2014/031071, filed on Mar. 18, 2014.

(60) Provisional application No. 61/803,039, filed on Mar. 18, 2013.

(51) Int. Cl.
*G06F 16/00* (2019.01)
*G06F 16/9038* (2019.01)
*G06F 16/951* (2019.01)
*G06F 16/901* (2019.01)
*G06Q 30/06* (2012.01)
*G06Q 50/00* (2012.01)
*G06F 19/00* (2018.01)

(52) U.S. Cl.
CPC ...... *G06F 16/9038* (2019.01); *G06F 16/9024* (2019.01); *G06F 16/951* (2019.01); *G06Q 30/0631* (2013.01); *G06Q 50/01* (2013.01); *G06F 19/3418* (2013.01)

(58) Field of Classification Search
CPC ......... G06F 17/30958; G06F 17/30991; G06F 17/30864; G06F 16/9038; G06F 16/951; G06F 16/9024; G06F 19/3418; G06Q 30/0631; G06Q 50/01
USPC ........................................................ 707/798
See application file for complete search history.

(56) References Cited

U.S. PATENT DOCUMENTS 9,755,842 B2 *   9/2017 Raleigh .................. H04L 12/14
2007/0219059 A1   9/2007 Schwartz et al.
(Continued)

OTHER PUBLICATIONS

United States Patent and Trademark Office (USPTO), International Search Report and Written Opinion, PCT/US2014/031071, dated Aug. 27, 2014, pp. 1-7, with claims searched, pp. 8-17, counterpart to the application filed herein.

(Continued)

*Primary Examiner* — Vincent F Boccio
(74) *Attorney, Agent, or Firm* — O'Banion & Ritchey LLP; John P. O'Banion

(57) ABSTRACT

Social graph based information recommendation engines, devices, systems and methods are described where information of interest can be retrieved and provided to a user based on sensor input and profile or preference information about the user or about a person other than the user.

24 Claims, 11 Drawing Sheets

(56) References Cited

U.S. PATENT DOCUMENTS

| | | | |
|---|---|---|---|
| 2008/0172362 A1* | 7/2008 | Shacham | G06F 17/30696 |
| | | | 707/999.003 |
| 2009/0106040 A1 | 4/2009 | Jones | |
| 2011/0164163 A1* | 7/2011 | Bilbrey | G06F 1/1694 |
| | | | 345/173 |
| 2012/0203640 A1 | 8/2012 | Karmarkar et al. | |
| 2012/0212400 A1 | 8/2012 | Border et al. | |
| 2012/0271831 A1 | 10/2012 | Narayanan et al. | |
| 2012/0278722 A1* | 11/2012 | Raleigh | H04L 12/14 |
| | | | 715/735 |
| 2012/0294495 A1 | 11/2012 | Wren et al. | |
| 2013/0018954 A1 | 1/2013 | Cheng | |
| 2013/0044130 A1 | 2/2013 | Geisner et al. | |
| 2013/0048720 A1* | 2/2013 | Lewis | G07C 9/00079 |
| | | | 707/803 |
| 2013/0085345 A1 | 4/2013 | Geisner et al. | |
| 2014/0099623 A1* | 4/2014 | Amit | G06F 17/30958 |
| | | | 707/798 |
| 2014/0168243 A1* | 6/2014 | Huang | G06T 1/20 |
| | | | 345/522 |

OTHER PUBLICATIONS

European Patent Office (EPO), extended European search report, related EP Application No. 14768589.5, dated Jun. 9, 2016, pp. 1-10, with claims searched, pp. 11-12.
State Intellectual Property Office of the People's Republic of China, Notification of First Office Action dated May 18, 2018, related Chinese patent application No. 201480012540.X, pp. 1-13, partial English-language translation, pp. 15-24, English-language claims examined, pp. 25-34.

* cited by examiner

| # | User | Location | Time | File | Text |
|---|------|----------|------|------|------|
| 1 | 001 | lat. XXX lon. YYY | YYMMDD Time | xx.jpg | Washington Monument is great! |
| 2 | 002 | lat. XXX lon. ZZZ | YYMMDD TTTT | yy.mp4 | Wow! I am running on the National Mall! |
| 3 | 004 | — | YYMMDD TTTT | — | You run very fast! |
| 4 | 001 | lat. XXX lon. YYY | | xx.jpg | Another good picture of D.C. |
| 5 | 010 | — | YYMMDD TTTT | — | I like your picture of the Washington Monument |

FIG. 13

US 10,346,480 B2

SYSTEMS, APPARATUS, AND METHODS FOR SOCIAL GRAPH BASED RECOMMENDATION

CROSS-REFERENCE TO RELATED APPLICATIONS

This application is a 35 U.S.C. § 111(a) continuation of PCT international application number PCT/US2014/031071 filed on Mar. 18, 2014, incorporated herein by reference in its entirety, which claims priority to, and the benefit of, U.S. provisional patent application Ser. No. 61/803,039 filed on Mar. 18, 2013, incorporated herein by reference in its entirety. Priority is claimed to each of the foregoing applications.

The above-referenced PCT international application was published as PCT International Publication No. WO/2014/153352 on Sep. 25, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to social graphs, and more particularly to methods for making social graph based recommendations and related systems and devices.

2. Discussion

Social graph technology links people, places and things. A social "graph" is not a graph in a mathematical sense, but is a diagram that illustrates interconnection among, for example, people in a social network. Each individual in the social network is called a "node" and a line between two nodes showing their interconnection is called an "edge". The "edges", or Interdependencies, can be based on, for example, relationships, age, gender, race, genealogy, financial transactions, trade relationships, political affiliations, club memberships, occupation, education, economic status and more.

While many different implementations of social graph technology exist today, a single comprehensive social graph does not exist. Therefore, developers build on existing technologies in an attempt to implement social graph technology that provides sufficient information to represent all possible nodes and edges.

BRIEF SUMMARY

This disclosure describes methods, systems and devices for social graph based recommendation. Improvements to social graph based technology are described, as well as using those improvements for making recommendations to a user. Systems and devices are also described that can make use of the social graph based recommendations.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 13 shows an example of how the information in FIG. 12 can be organized in a database for retrieval using the process illustrated in FIG. 11A and FIG. 11B.

DETAILED DESCRIPTION

A. Social Graph Technology

Figure 1:
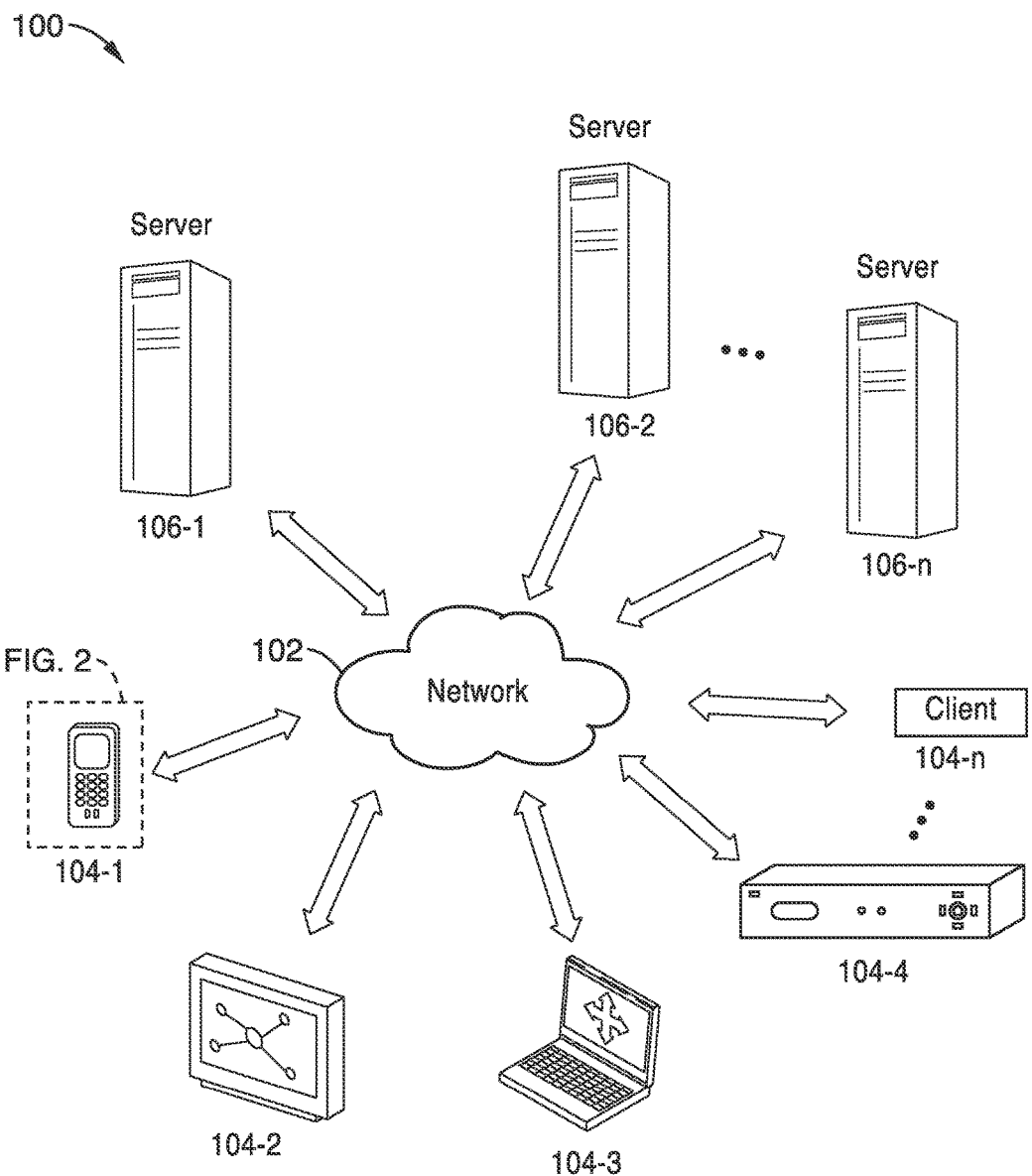
FIG. 1 is a schematic diagram of an embodiment of a social graph based recommendation system described herein.

A social graph is a network of relationships depicted pictorially as multiple circled numbers called nodes that are connected to depict inter-nodal relationships (interdependencies) through lines called links or "edges". Social graph technology collects, filters and/or displays content to users through social channels. Content can include, for example, music, video, games, pictures, articles, news, and books. Social channel content can be presented to a user through, for example, web sites, mobile apps, text messages, blogs, e-mail digests, RSS feeds, TV/tablet synchronized to display respectively relevant information of each (i.e., a second screen), and other vehicles.

B. Improvements to Social Graph Technology

Several challenges exist with social graph technology. One challenge relates to filtering, such as how to share content with other people in a personalized manner. For example, a user may not want to receive all content from a specific member of their social network. Another challenge relates to creating serendipity, such as how to share content with people who have not expressed interest in this content but are likely to be interested. Still another challenge relates to maintaining privacy, such as how much information should be shared with whom and the level of trust related to the person with whom the information is to be shared. Another challenge relates to how social channel environments are forged. Currently, different services are used for different social channel purposes, and different platforms are used with those services.

C. Social Graph Based Recommendation Engine

Better social graphs can be generated by taking into account various categories and items of information through the use of a recommendation engine according to various aspects of the technology described in this disclosure. For example, a user's profile setting could be parsed for information such as age, gender, user preferences, school information, which artists the user likes, where the user works, where the user was born, etc. The user's location can be considered by, for example (i) detecting absolute location information (e.g., triangulation, GPS, WiFi position, check-in information, and (ii) detecting relative proximity of distance and time (GPS, NFC, WiFi Positioning, environmental sound analysis, etc.). As an example of environmental sound analysis, when a similar sound wave is detected in a plurality of devices in the same vicinity, they could be assumed to be in the same area. Similarity can be found by analyzing sound wave using, e.g., Fourier transform. The user's personal timeline could be taken into account, such as past (e.g., where the user had lunch yesterday, present (e.g., where the user is currently drinking coffee), and future (e.g., the user's plans to go to a high school reunion in two weeks). User specific likes/dislikes (e.g., user-specific ratings) can be considered. For example, a computer system could accumulate the user's "like" history and analyzes the contents "like"ed. The system could retrieve preference information by using meta data attached to the contents "like"ed. Then, the system highlights contents whose meta data, at least partially, matches the user's preference information. Keywords of the information feeds received/sent by the user could be taken into account. Another consideration could be the types of apps used by the user and the user and the amount of time spent on those apps. For example, if a photo sharing app is installed and heavily used, then perhaps it can be assumed that the user is interested in how to take a good picture or what type of filter should be used to improve a picture. What the user's friends (or a subset of friends) care about can be considered. Additional considerations could be the type of pictures/videos taken (e.g., many pictures/videos of the same children assume the user may have children and is interested in parenting content).

Better social graphs could be generated by taking into account the user's willingness to allow for serendipity, e.g., show content posted by people, whom the user is not directly connected to in a social channel but who have common friends with the same interest. Preferences/profile information can be used to make a more likely accurate social graph recommendation. For example, the system could analyze the social distance (how many nodes are there between two people) and the similarity of preference between them. Like this, preference information, which may be used with other information, can be used to select content that is likely to be interesting. Another example would be that the user asks the social channel to decide to whom they should be connected or perhaps "I am feeling lucky". A further example would be that the user would like to know whether people on a beach are interested in playing volleyball in 15 minutes. Still another example would be that a male user wants to know whether any other females who are also at a cafe are interested in meeting to discuss classic literature over a cup of coffee.

Metadata attached to web sites/blogs visited by the user could also be used to generate better social graphs. Such metadata could include, for example, (i) which web sites/blogs are often visited by the user, (ii) the amount of time spent on the web sites/blogs, and (iii) associated trackback links (e.g., which web sites are linking to which articles).

The user's application of filters could also be used. Examples of such filters could be (i) the user does not want to see family photos of a certain friend on a social network, (ii) the user does not want to see status of a friend's Farmville progress, (iii) the user wants to see which friends are visiting New York, and (iv) the user does not want anyone nearby to request a meeting. A child's parents could determine to filter out age-appropriate information.

Sensor information coming from a device, such as a touch screen or camera installed in a mobile phone could be used to generate better social graphs. For example, the touch screen measures how much time a user continues to touch a handheld's screen when checking a web site/game. If the site/game requires continues contact with the screen then it shows that the user may not be that interested. Other sites/apps may provide indicative information if the user slides their finger slowly on the touch screen.

Statistical data could be used as well. Examples include (i) information that is trending generally (e.g., a significant percentage of users in a social channel are listening to a new song) and (ii) financial data associated with content (e.g., the amount of money generated to date by a movie), (iii) information deemed to be important by e.g., 1) at least a certain number of users tagged that information to be important; 2) a news source such as CNN determined that a certain news story was important. Obsolescence rate could be taken into account, such as a posting that remains relevant over time may be deemed more useful. Ratings determined by a social channel (e.g., percentage of users on a movie review website liked a certain movie) could also be taken into account.

Still further factors that can be taken into account for generating better social graphs include, but are not limited to, the following:

(a) Tags associated with music, video, pictures, articles, news, and book content (e.g., jazz listed as the genre of music for a certain song);

(b) A social network's application of filters to reduce noise (e.g., spam, pornography);

(c) Server-side log data (e.g., content, which is similar to or within the same category as ones you purchased or reviewed previously, could be recommended to the user);

(d) Detecting strength of relationship on network (e.g., time that people played on-line game together, similarity of playing music/movies, etc.);

(e) The size of a relevant social network (maybe just pairs of people in a sub-group in a social channel?);

(f) The type of social channel that is being used (e.g., geared towards professional relationships or more personal ones); and (g) Human sensory information. Human beings have five senses, and the senses could be leveraged to help build a better social graph. The five senses are sight, hearing, taste, touch, and smell. For example, vibrating a phone, flashing a light, making a sound, sending a signal for a separate but nearby device to emit odors, or sending a signal to the user's refrigerator to suggest that the user drink a particular brand of beverage could be employed.

Music-related factors can also be used to generate better social graphs. Such factors could include, for example, genre, artist, similar songs, similar artists, tags, a user's mood, ratings, music from friends, music from experts, new releases, music shared on a local network, preference for streamed versus local files, music file signature for files or for live events such as somebody humming, history of listening within a social channel, history of listening across social channels, history of a user's friends' history, most listened/liked, trending music, old time favorites (stay popular over time), and recognition from movement/gesture (visual), humming (audible), etc.

Similarly, video-related factors can be taken into account. Such factors could include, for example, genres, tags, ratings, additional related information for professional content, actors, pictures, ratings, friends who also watched, history of viewing which allows recommendations of new content for discovery, chatting with friends who are checked into a TV show, etc.

The specific algorithms for generating better social content would be based on the factors to be considered and could be readily developed by one skilled in the art that is provided with the factors.

An example of an algorithm would be to use location information to judge that people who are in the same place for a long time have a good relationship. However, location information alone may not be enough to judge human relationship. Therefore, other factors should be included as well. For example, if the people sit together in a train, the people will be detected as having some relationship though they are not even acquaintances with each other. Accordingly, there is a need for automatic social graph generation based on factors other than location alone.

The algorithms could be structured to automatically generate and update the social graph, particularly human relationship information (e.g., friend, acquaintance, friendship level etc.). For example, an algorithm could be designed such that when a user checks in at a particular jazz club in New York and modern Jazz is being performed at the time the user checks-in, it is assumed by the algorithm that there is a connection between the user being at that jazz club at the time of the performance of modern jazz, and the user's interest in listening to or exploring modern jazz. A modern jazz tag could then be flagged for that user.

Additional examples for algorithms include:

(a) Updating relationships of people who play on-line games a lot.

(b) Judging relationship level as strong when people email each other on holidays.

(c) Dynamically changing the order of reproducing music, whereby songs that receive many "Like"s will be reproduced sooner than others.

(d) Creating a collective jukebox based on the playlists of users in a bar by reading each patron's playlist and determining which artists, genre, songs, etc. the collective users like/listen too frequently.

(e) Determining the preferences of the majority of the listeners and play the songs that appear with the highest frequency.

(f) Making recommendations to users looking for other content.

(g) Pushing content in response to a user selecting preferences.

(h) Pushing content to a user even though the user does not know they are looking for the content.

(i) Queuing information in a timeline, which will be presented to the user in order when the user logs into the social channel.

It will also be appreciated that the results generated from social graphs could be presented to users in various ways.

For example, for music and video, a social channel may be a streaming service. Users who do not like actively inputting settings could enjoy passive listening/watching. A TV or tablet could be synchronized to display respectively relevant information of each (i.e., a second screen). Presentation of pictures, articles and news could be in the form of a slide show or list of content.

D. Generalized System Implementation

It will be appreciated that a social graph based recommendation engine would be associated with a "smart" device that is a client device in a networked infrastructure. In the generalized embodiment shown in FIG. 1, there is shown a networked infrastructure (e.g., system) 100 that includes a network 102 such as the Internet. One or more client devices 104-1 through 104-*n* would communicate with the network by means of a wired or wireless connection. The system would also include one or more servers 106-1 through 106-*n*, such as, for example, social media servers, news servers, data servers, encyclopedia servers, and servers hosting user profiles, that are connected to the network through wired or wireless connections. The servers may include standalone servers, cluster servers, networked servers, or servers connected in an array to function like a large computer. The client devices 104-1 through 104-*n* can be any conventional "smart" device with a processor, associated operating system, and a communications interface. Examples include a Smartphone 104-1, a tablet 104-2, a computer 104-3, and a set top box 104-4.

Figure 2:
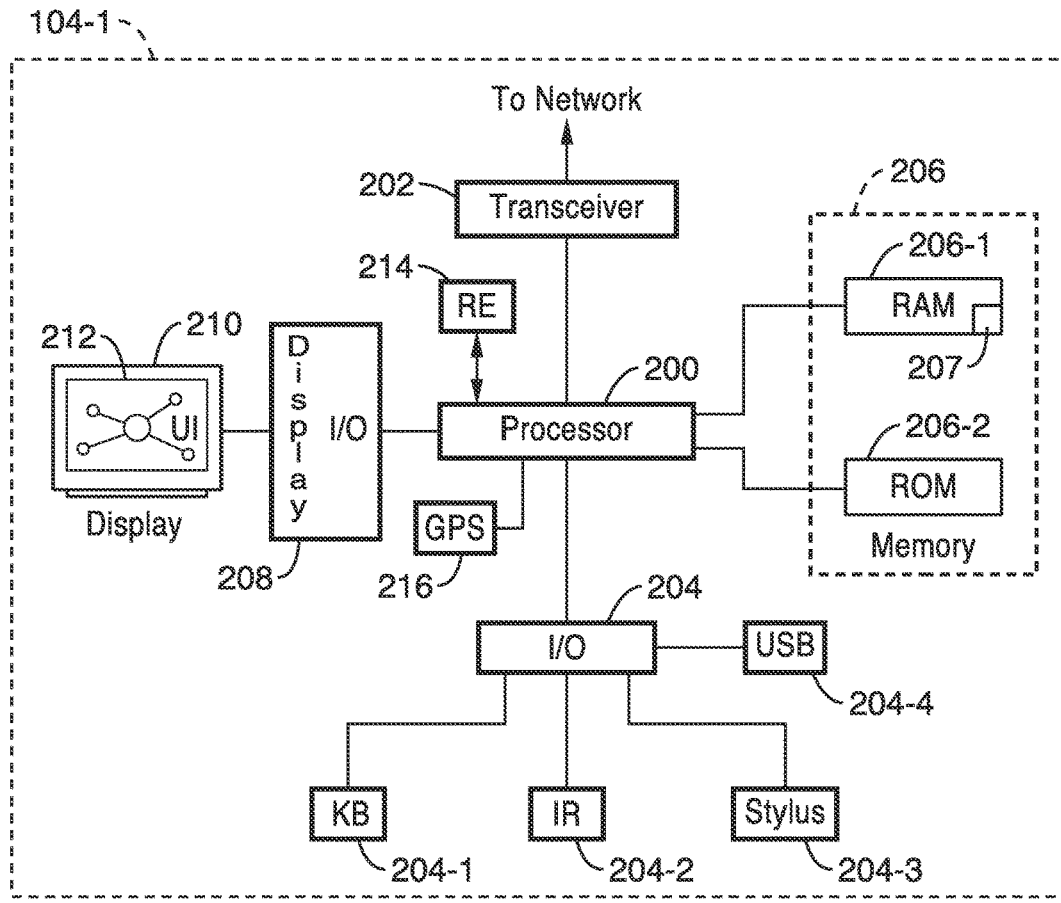
FIG. 2 is a functional block diagram of an embodiment of a smart device with a recommendation engine described herein.

FIG. 2 illustrates how a smartphone device 104-1 may be configured. In the exemplary configuration shown, the device includes a processor 200, a wireless communications transceiver 202 for network communications (e.g., Bluetooth, WiFi, cellular, near field communication (NFC) or pairing with a cellular device), an input/output controller 204 for communicating with one or more input output devices such as a keyboard 204-1, infrared communications device 204-2, stylus pad 204-3, and USB port 204-4. The device also includes memory 206 which may include RAM type memory 206-1 and ROM type memory 206-2. The RAM type memory may have a storage space 207 for storing application programming. A display input/output controller 208 would typically be provided for communicating with a visual display device 210 that may also have a user interface 212 such as a touch screen display. A recommendation engine 214 could reside as an executable program in the device for implementing social graph based recommendations. A GPS communications device 216 could also be included to provide location information to the recommendation engine for use as a factor in the social graph technology.

Figure 3:
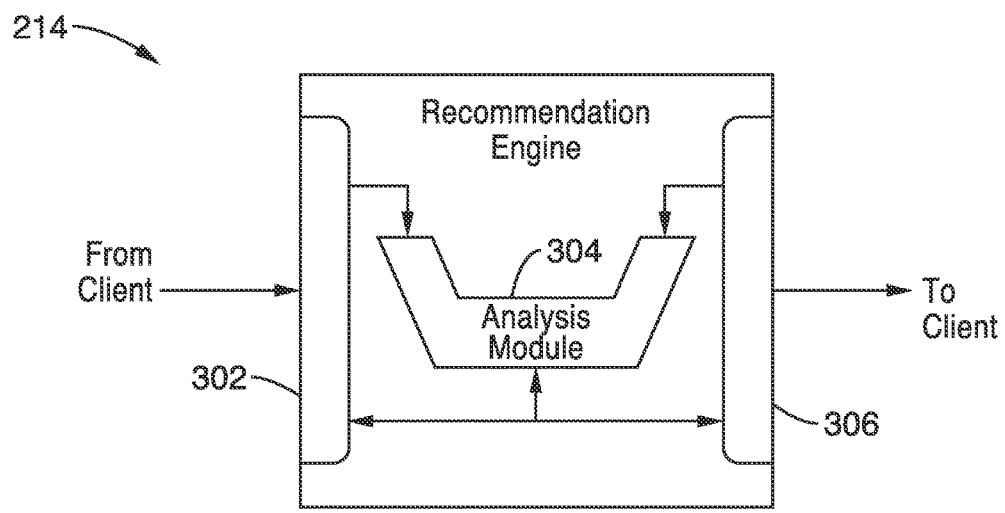
FIG. 3 is a functional block diagram of an embodiment of a recommendation engine described herein.
Figure 4:
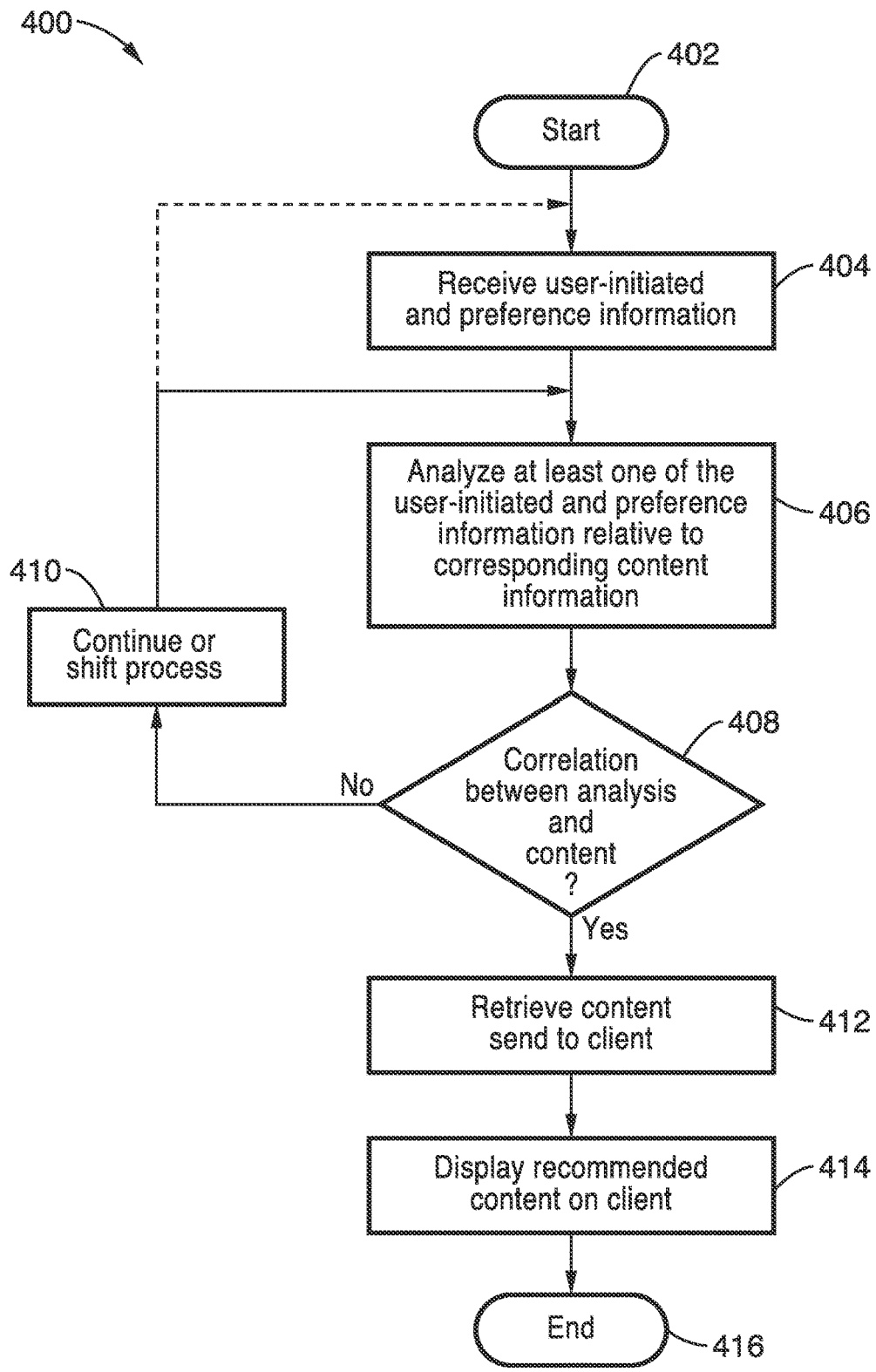
FIG. 4 is a flow chart of an embodiment of a recommendation process described herein.

FIG. 3 illustrates an embodiment of the architecture of a recommendation engine 214 that could be used in the smart device 104-1. The recommendation engine would, for example, receive input information 302 from the device, process that information with programming in an analysis module 304, and provide output information 306 to the device. FIG. 4 illustrates an example of a processing algorithm 400 for the recommendation engine. Processing would start at block 402 and user-initiated and preference information would be received at block 404. At block 406, at least one of the user initiated and preference information would be analyzed relative to corresponding content information. If there is no correlation between the foregoing analysis and content 408, then the process would proceed to block 410 and either loop back to block 406 or start over at block 404. If there is a correlation, then the recommended content would be retrieved at block 412 and displayed to the user at block 414. The process would then end at block 416.

E. Smart Head Worn Device Example

Figure 5:
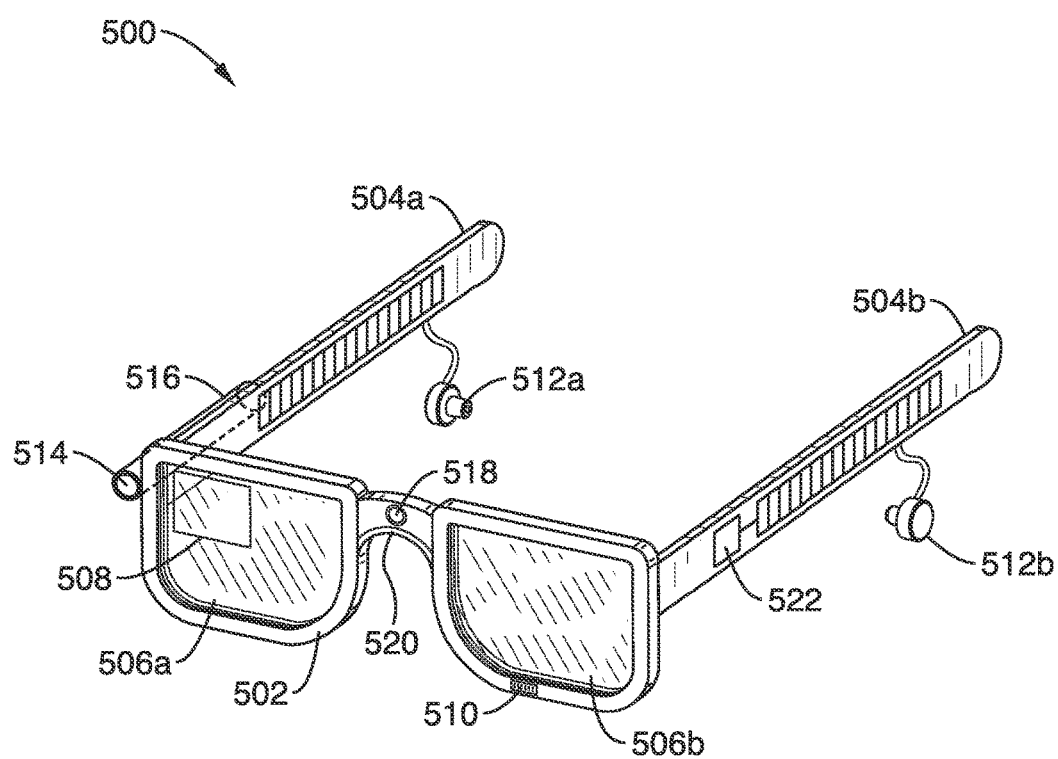
FIG. 5 is an embodiment of a "smart glasses" device described herein.
Figure 6:
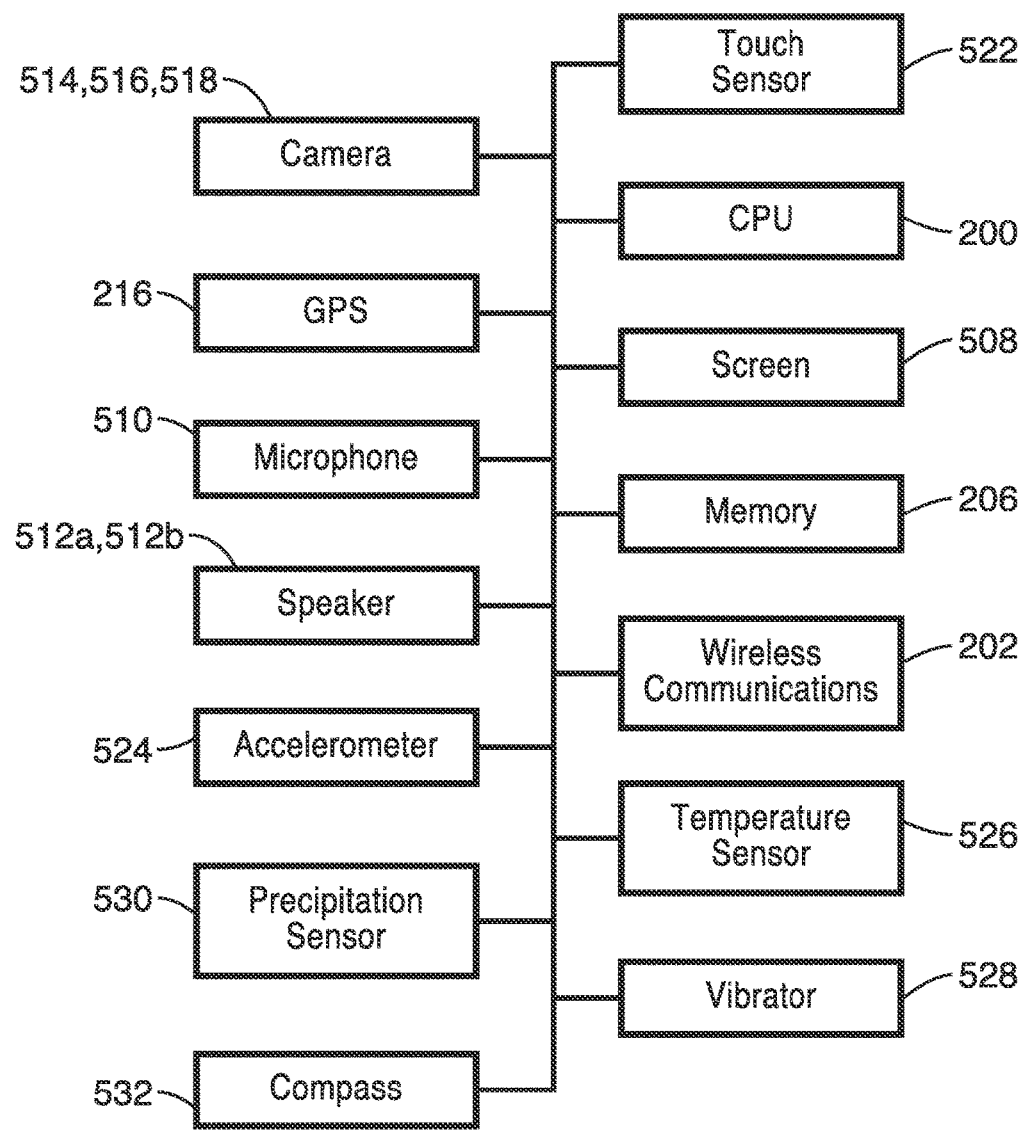
FIG. 6 is a block diagram illustrating various components that can be used in the device shown in FIG. 5.

In one embodiment, the social graph based recommendation technology described herein can be implemented in a head worn apparatus 500 such as illustrated in the example shown in FIG. 5 and FIG. 6. In this "smart glasses" embodiment, the apparatus comprises a frame 502, frame supports 504a, 504b, and lenses 506a, 506b arranged in an eyeglass configuration. The apparatus could also be configured on other ways such as, for example, waterproof goggles for underwater use.

The apparatus may include a display screen 508, a microphone 510, speakers 512a, 512b, a front-facing camera 514 for a forward view, a rear-facing camera 516 for a rearward view, a forward- or rear-facing camera 518 on the nose bridge 520 for monitoring facial expressions and/or eye conditions, and a switch 522. Note that the cameras can be any combination of video or still cameras, and may include a fisheye lens. The display screen would preferably be an OLED type through which the user can see. The switch could, for example, be a touch-sensor switch for compactness. Also, the manner of attachment of the foregoing components and exact positioning could be varied without departing from the technology described herein.

Referring also to FIG. 6, it will be appreciated that the apparatus may include a wireless communications interface (e.g., transceiver) 202, as previously described, and a processor 200, with associated memory 206 and recommendation engine 214 as previously described. A power supply (not shown) for the various components may also be included with the apparatus. Optionally, the apparatus may include one or more components selected from the group of a GPS device 216 as previously described, an accelerometer 524, a temperature sensor 526, a vibrator 528, a precipitation sensor 530, and a compass 532. Other devices and sensors may be included as well. These components may be external to the frame and support arms, integrated or embedded in the frame and/or support arms, or a combination thereof.

The cameras can be used to collect visual data and the microphone can be used to collect audio data, both of which can be sent to a server. Camera 518 on the nose bridge could collect visual data which is used in combination with iris detection technology to determine the identity of the user of the apparatus in order to log the user into his/her profile. Other ways may be used to log the user into his/her profile such as audio recognition, other biometric methods or more traditional ways of logging a user into his/her profile such as the entry of a user name and password.

Camera 518 could also be used to collect visual data about the user such as a certain facial pattern or eye pattern (e.g., pupils dilated when the user detects something appealing) in order to upload the information to a server for social graph calculations.

In another embodiment, the apparatus may include a camera on the inner side of each of the frame supports for detecting whether or not the user winks. In a still further embodiment, a biometric sensor may be included on the inner side of each of the frame support and positioned so that the sensor will be near the temple of the user when the apparatus is worn. For example, the sensor could be used to detect and display heart rate, body temperature etc.

F. Applications

1. Tourist Mode

Figure 7:
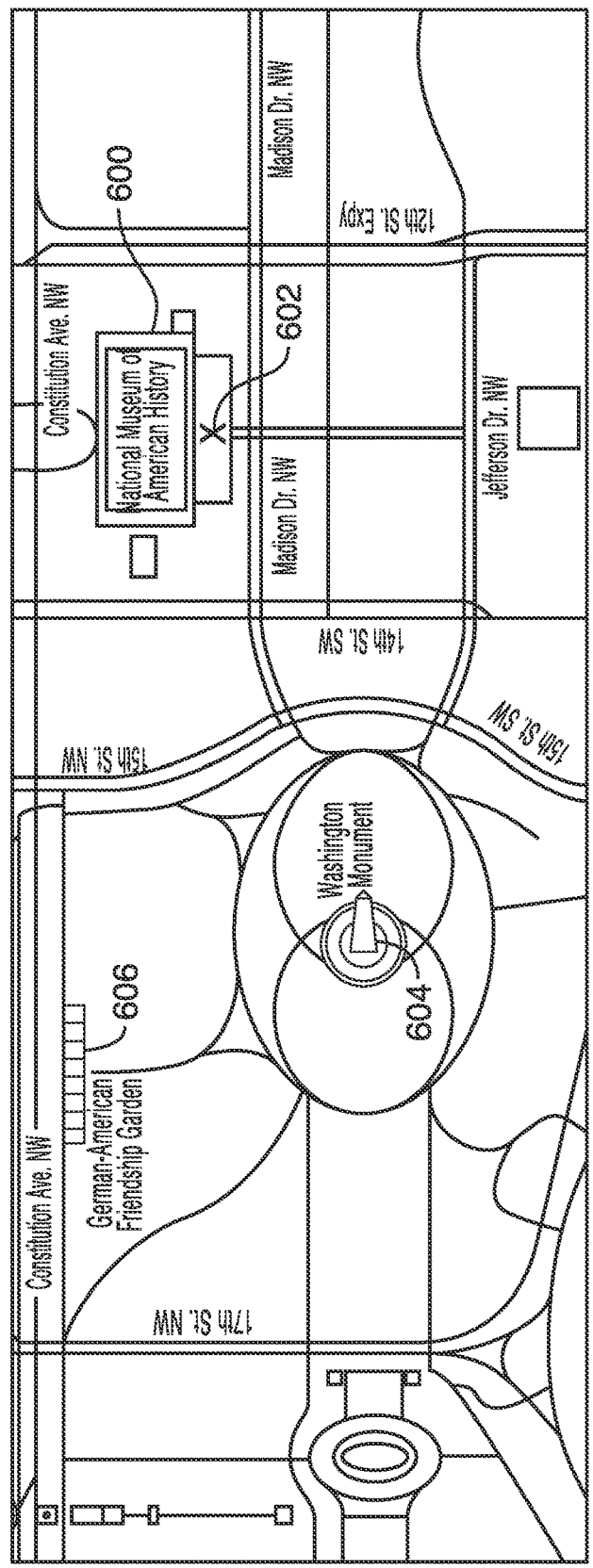
FIG. 7 is an image of the Washington mall used in an example of a recommendation process described herein.
Figure 8:
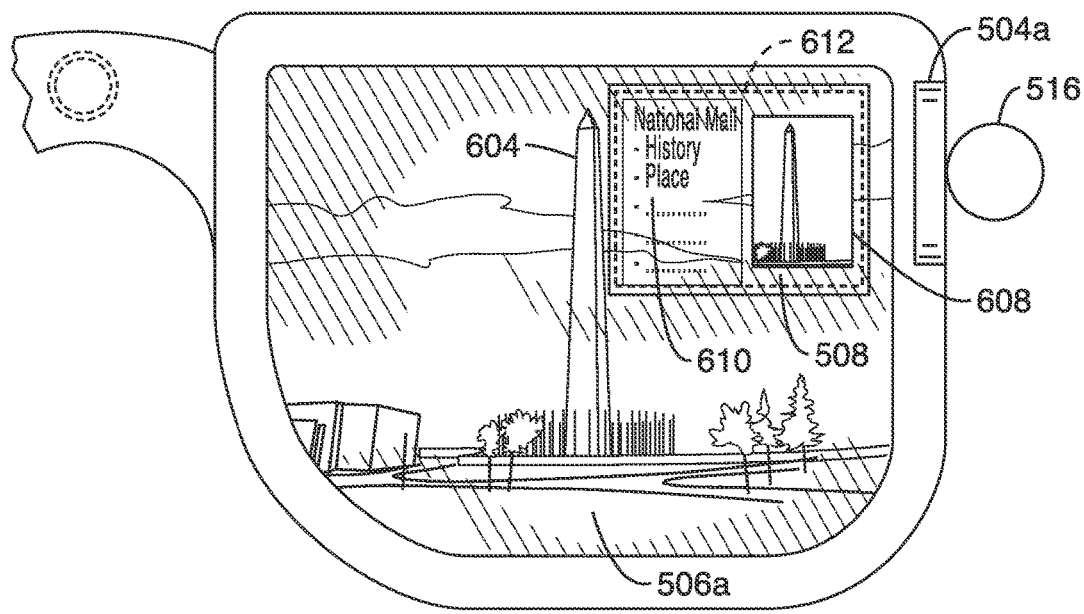
FIG. 8 and FIG. 9 illustrate an example of how the recommendation engine described herein can display information of interest to a user when viewing an object with the device shown in FIG. 5.
Figure 9:
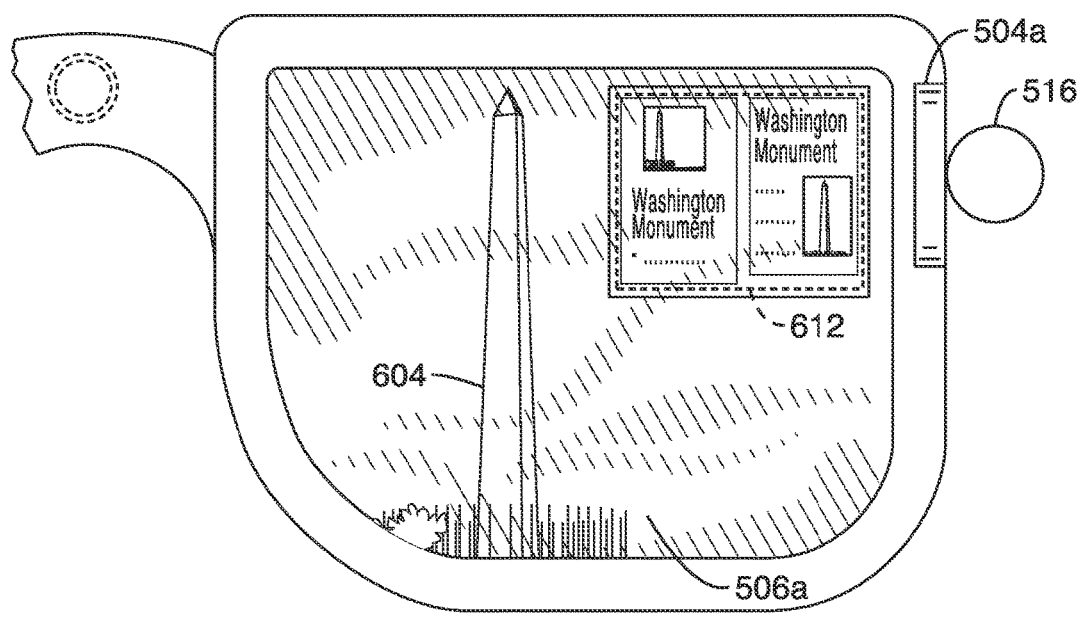

Referring now to FIG. 7 through FIG. 9, in an example of one mode of using the apparatus, a user receives audio and visual data about a site seeing tour. The apparatus would capture images through the video cameras, capture audio through the microphone, and capture position, direction and other information through the compass, GPS and other sensors, in order to determine what the user is observing. For example, suppose that the user is standing in front of the National Museum of American History 600 (the user's position 602 marked as an "X"). Further suppose that the user is closest to the National Museum of American History, but the user is facing the Washington Monument 604. Now, suppose that the user wants the apparatus to provide information about the Washington Monument even though the user is closest to the National Museum of American History. The apparatus uses its sensor information to determine (1) the location based position of the user through, for example, GPS, (2) the video and/or still image data of what is in the visual field of view of the front facing camera in the apparatus; (3) compass information which detects the direction that the user is facing; and (4) other information.

All of the information that is collected by the apparatus would be transmitted to a server in the cloud (e.g., Internet connected remote server) which would then determine that the user is facing the Washington Monument and would likely want to receive information about the Washington Monument. The information is sent back to the apparatus and a video and/or image data 608 and/or text data 610 and/or audio data (collectively, "Presentation Data" 612) (see FIG. 8 and FIG. 9) is presented to the user via the screen 508 located on the apparatus. Furthermore, the user's social graph profile settings may indicate that the user is interested in historical information about famous sites and so the Presentation Data could be geared towards historical information about the Washington Monument. Alternatively, the user could be interested in architecture and so the Presentation Data could be geared towards the monument's architectural significance. Alternatively, the user's profile could show that the user is in grammar school and that the user recently studied about George Washington and so the Presentation Data could be geared towards the grade level of the user and perhaps incorporate information about George Washington.

The Presentation Data may be very interesting to the user and the user may want to post the information onto a social media channel. On the other hand, a user who is in grammar school may not want the Presentation Data to be posted to his/her social media channel (e.g., facebook). Instead, the user may want the Presentation Data to be stored in the cloud for later use in a report, presentation or own personal timeline concerning the user's trip to Washington, D.C. In either scenario, the user may want to regulate what information is posted onto facebook or other social media channels by instructing the apparatus accordingly.

Further suppose that a user does not want to be bothered by boring information. The system could be configured such that the more a user wears the apparatus, the more the apparatus (e.g., via the server/cloud/social graph analysis) learns about the user and is then better able to use analytical processing techniques to filter out information that may not be as interesting to the user.

Again, using the Washington Monument example, and referring to FIG. 7, suppose that the user is facing the German-American Friendship Garden 606 but the recommendation engine determines based on the user's social graph profile factors that the user is not interested in gardens. In that case, the Presentation Data information is not presented to the user.

In another embodiment, the Presentation Data could pertain to live objects (e.g., people, pets) within the field of view of the apparatus rather than about physical objects such as the Washington Monument. For example, if a person within the field of view of the user's apparatus has a smart device, then data about that person could be transmitted from the server/cloud/social media channel down to the user's apparatus to display whatever information is available about that other person through the social media channel and is accessible by the user's social graph.

Figure 10:
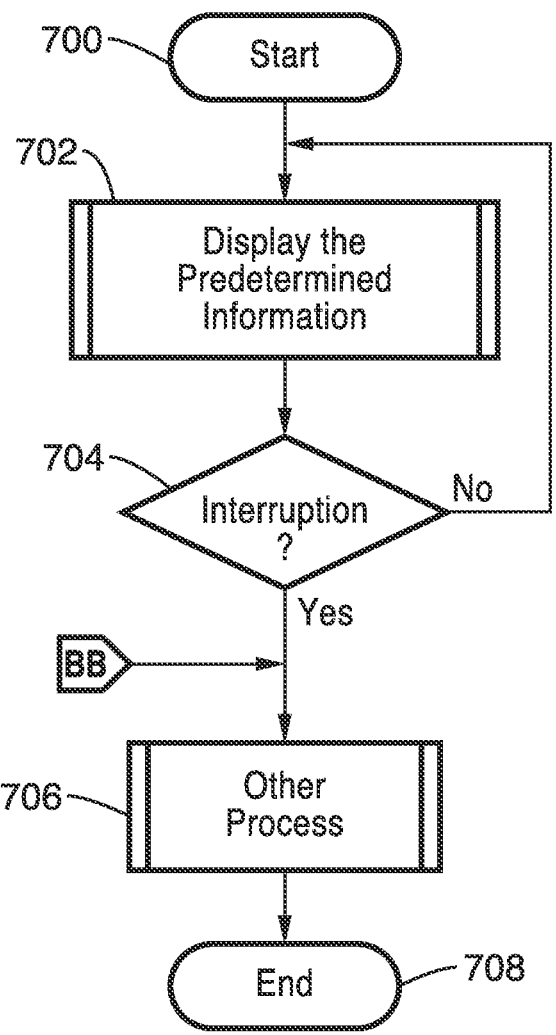
FIG. 10 is a flow chart of an embodiment of an information display process that can be used with the device shown in FIG. 5
Figure 11A:
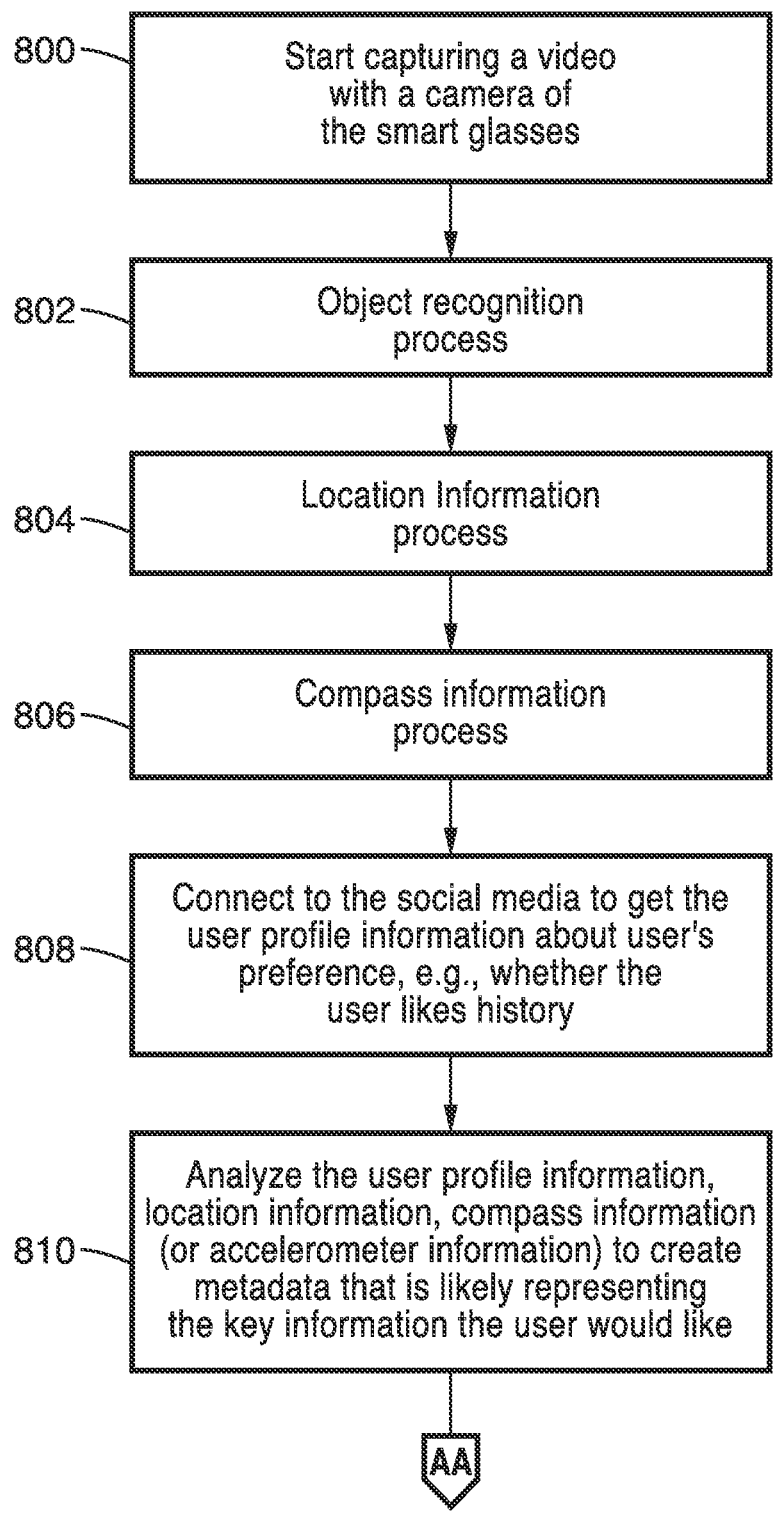
FIG. 11A and FIG. 11B are a flow chart of an embodiment of a recommendation process that can be used with the device shown in FIG. 5.
Figure 11B:
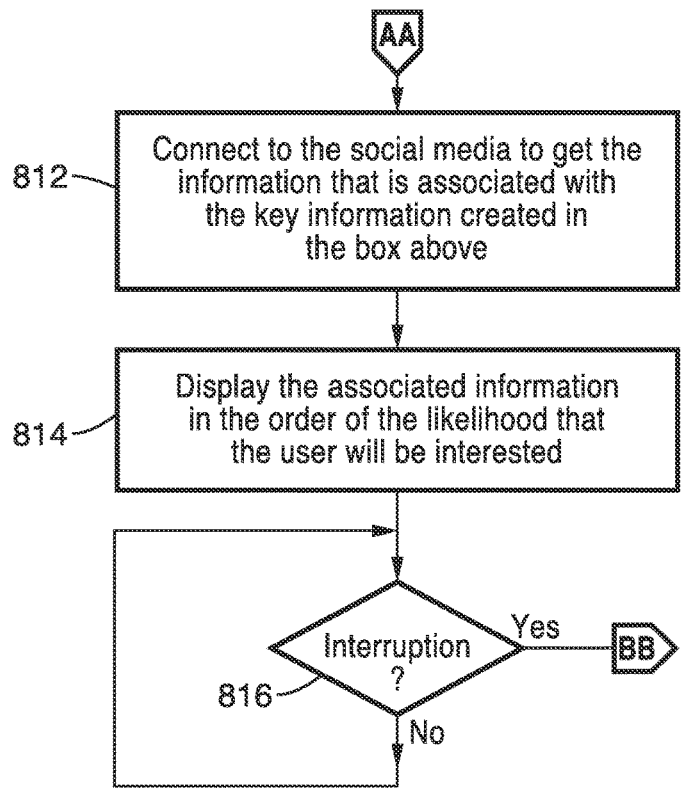

FIG. 10, FIG. 11A, and FIG. 11B provide an example of how the tourist mode could be initiated and function. First, referring to FIG. 10, a "general" mode of operation starts at block 700. Next, at block 702, predetermined information is displayed to the user. Such information could include, for example, time, a pre-set picture, weather information, and/or status of a cell phone that is paired to the apparatus. At block 704, the device checks for an interruption event. An interruption event can include, for example, the occurrence of a particular time, a user activity, a preprogrammed interruption, or a scheduled interruption. A user interruption could include, for example, touching the touch sensor 522 (FIG. 5), speaking a command or phrase (with speech recognition), or the user taking a picture. If there is no interruption event, then the process repeats by looping to block 702. Otherwise, another process could be executed at block 706, with the entire routine ending at block 708.

In this example, the "other process" at block 706 is operation of the tourist mode described above, and illustrated in detail in FIG. 11A and FIG. 11B. In this case, as the apparatus populates the display with information that is likely to be interesting to the user based on, for example, user profile information. The user touches the touch sensor 522 (FIG. 5) to manually instruct the apparatus to start the tourist mode. At block 800, the apparatus then captures video with one or more of the cameras and an object recognition process 802, location information process 804, and compass information process 806 are carried out. The location information process would, for example, calculate the user's location using GPS or other information such as cellular tower location(s). Other processes could be carried out as well, including sensing movement with an accelerometer.

At block 808, the device connects to one or more social media servers to obtain the user's profile and information about the user's likes, dislikes, history, etc. Next, at block 810, the user's profile information, location information, compass information, accelerometer information, etc. are analyzed to create meta data that is likely to represent the key information that the user would like to have presented on the display. At block 812 the apparatus connections to a social medial server to retrieve the information associated with the analysis in the preceding block. Then, at block 814, the retrieved information is displayed to the user. After the information is displayed to the user, a test for an interruption could even be made at block 816. If no interruption event is found, then the apparatus continues to display information. Otherwise, the display process exits and operation returns to block 706 (FIG. 10) for execution of another process. An interruption event could include for example, a timer that is set for displaying new information periodically based on updated objection recognition information. Other examples include detection of a new object, detection of user facial expressions, detection of new location information, distance associated with a change in location, or the timing of detecting any of the foregoing.

It will be appreciated that the screen size of the display 508 (FIG. 5) will be limited, so information preferably should be displayed efficiently. In one embodiment, the information should be selected by the user preference information such as profile information the user creates in his or her account at the social media provider (for example, facebook). For example, if the social media provider identifies the three most interesting areas of the user, only the information related to those three areas should be displayed on the screen.

Suppose, for example, that the three most interesting areas are (1) history, (2) food and (3) modern art. In the case where the above described tourist mode is activated, the apparatus may use a location based social media service (e.g., Four square) to search the information for which the user is likely interested. For example, when the user turns on the tourist mode while observing the Washington Monument while standing close to National Museum of American History, the apparatus could search for the check-in information of other users who have checked-in so far on the location based social media service.

The user's apparatus could then sort the check-in information of the other users in the order of the above (1) history (2) food and (3) modern art. The sorting process could be carried out by the processor in the apparatus or by that location based social media service (more specifically, by the servers hosting the service). Also, the sorting process may be split into a plurality of processes, and the apparatus or the servers of the location based social media services may process each of the split processes accordingly.

For example, the splitting process could be configured such the user's apparatus performs the processing for displaying the information to be displayed while the social media provider's servers perform the processing for searching for the information the user would get interested.

With regard to the process of searching for information of interest to the user, the process may be that the object viewed by the apparatus is analyzed first (e.g., using the local processor in the apparatus and/or the server of the network side). If, for example, the object is recognized as the Washington Monument, the local processor in the apparatus (optionally together with the servers) would analyze the tag information (e.g., meta data) of the Washington Monument on the social media servers. The local processor in the apparatus (optionally together with the social media servers) would find that the Washington Monument is historic architecture by the fact that, among tag information falling within the above-mentioned (1)(2)(3) categories, the historic key words (such as, 1800s, civil war) are most found on the social media services.

The local processor in the apparatus would then decide the order of the information to be displayed and display the history information first. Next, the local processor in the apparatus may search history related social media for Washington Monument related information. In this example, the information displayed on the screen would be richer than information provided solely by location based social media services.

In another example, Wikipedia may be first analyzed for the general information about the object that is identified. It may be the case that the one social media service has various types of information. In this case, the information on the social media service may be first sorted by the category of the information (e.g., history) to reduce the amount of processing required. In this way, the user can see the historic information displayed on the screen, rather than the irrelevant information. The information associated with the other two categories (e.g., food, modern art) based on the user's location also may be displayed on the screen. Preferably, however, the amount of space on the screen allocated for displaying such lower priority information would be smaller than the history information. The lower priority information may be displayed on the screen as an icon indicating the existence of such information (for example, blinking food icon indicates there is food information linked to the location).

Figure 12:
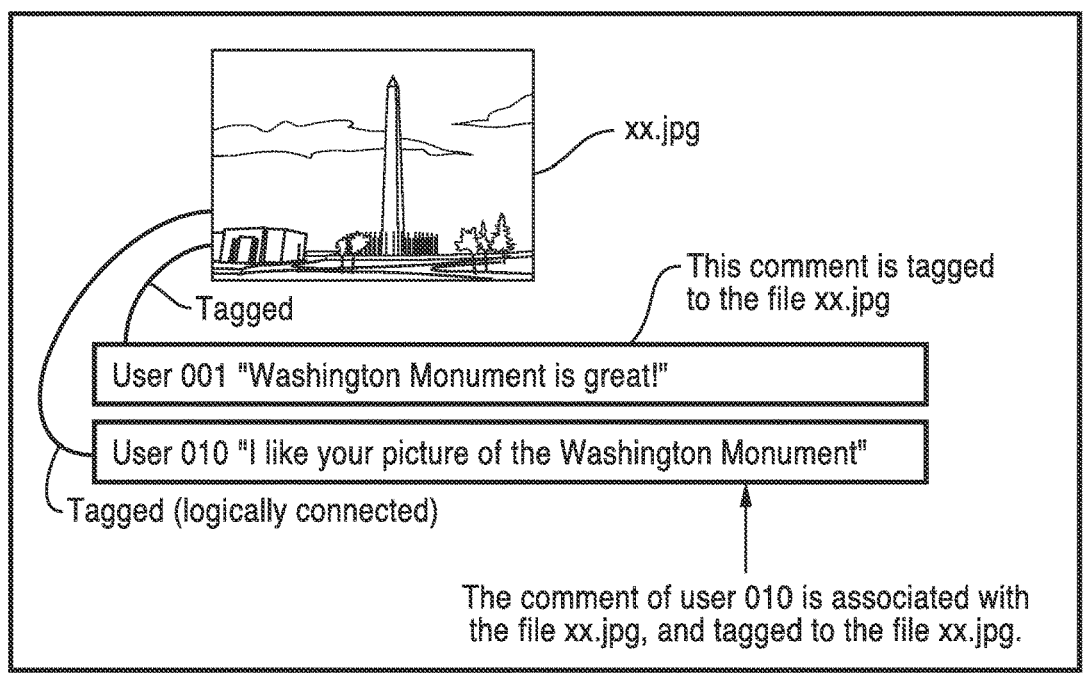
FIG. 12 shows an example of logical connections for information stored in social media for retrieval using the process illustrated in FIG. 11A and FIG. 11B.

Referring also to FIG. 12 and FIG. 13, examples of logical connections for information stored in social media and how the information could be organized in a database are shown, respectively. For example, FIG. 12 shows that the image data (x) is logically associated with user01's comment (y) and user02's comment (z). Suppose that a picture xx.jpg is posted on social media such as facebook. The image data is tagged (i.e., associated) with user01's comment (x) and user02's comment (y). FIG. 13 shows that each data entry has various metadata such as entry number, user ID (e.g., user 001, user 002 etc.), location (e.g., GPS information in the form of latitude and longitude, or ID of cell towers), time, file name of associated audio-visual files (e.g., image files, audio files, or video files) and written text. It will be appreciated that associated audio visual files would not necessarily be written in the database. In other words, a user's comment would not necessarily include associated audio-visual files.

When a user searches for relevant information stored on a social media server, the user will typically conduct a key word search. In the example shown in FIG. 13, by using the keywords "Washington monument", database entry numbers 1 and 5 will be retrieved and associated with a picture of the Washington monument as shown in FIG. 12. As result of this type of searching and retrieval, only relevant information will be displayed on the apparatus shown in FIG. 5.

2. Driving Example 1

In this embodiment, suppose that a user of the head worn apparatus is driving a car. One or more of the cameras could monitor the user's (the driver's) ability to stay awake while driving. Upon determination that the driver's alertness has decreased, the apparatus could send a signal to the car's sensors which would in turn emit a signal for the car to permit the emission of a smelling salt (e.g., ammonium carbonate, a colorless-to-white, crystalline solid ((NH4)2CO3.H2O)) or some other odor to invoke the driver to become more alert while driving. In addition, or alternatively, a loud noise could be emitted or the driver's car seat could be made to vibrate in order to alert the driver of the unsafe driving conditions. Some of the sensors may need to be located on the outside of the car to more accurately inform the driver of unsafe driving conditions, such as precipitation and/or temperature dropping below 32 degrees Fahrenheit.

3. Driving Example 2

The apparatus can also be configured to show augmented reality (AR) images on the display screen 508. The AR images can be stored in the memory 206 or can be downloaded in real time from a server. The user will see a AR image naturally superimposed on the display screen, which will help the user not to be interrupted by text or new images being displayed when the user is driving. In this embodiment, the display screen 508 preferably is an OLED type that is transparent when no image is shown so that the driver can see without his or her vision being obstructed.

4. Driving Example 3

In another embodiment, the apparatus is configured to detect that the user is present in the moving vehicle. For example, the apparatus may include sensors, such as accelerometers 524, and be programming to determine whether the user is in a car from a stored signal pattern associated with movement of the car. For example, if the apparatus finds a high frequency signal pattern that is unique to movement of a car, then the apparatus will know that the user is in a moving vehicle. Note that this approach could also be used to determine whether the user is walking, whether the user is on an elevator, whether the user is riding on a bicycle, for example. GPS information could be used to determine the speed of the user.

The programming could be configured to periodically take a picture using a camera on the apparatus and then process the picture by performing object recognition. For example, if the programming recognizes that an object in the picture is a wheel (as typically found on a car), and, in addition, GPS information indicates that the user is moving faster than the range of possible speeds of a human running and further indicates that the user is moving in the range of the speed of a car, then the programming might designate that the user is in a moving car. The relevant speed ranges could be stored in memory 206 or be downloaded from a server. In another embodiment, the programming may use a remote server to process the sensor information.

5. Driving Example 4

In another embodiment, the apparatus could include a "car mode"; that is, a particular mode of operation when the user is in a car. Car mode could be initiated by the user manually, or the apparatus could detect that the user is in a car. In car mode, the apparatus may change its operation depending on the user's activity. For example, in car mode the programming could reduce the brightness of the screen so that the user is less interrupted by the object shown on a screen while driving.

As another example, the programming could reduce the size of the screen displaying information when the user is driving. The benefit is that the user can see all of the things when he drives a car. For example, when the programming switches the apparatus into a car mode, the programming could modify the size of the display screen 508 so that 70% of the displayable area becomes inactivated. Important information would still be displayed to the user but with less obstruction of the user's view. In another embodiment, the apparatus could use a sound alert, vibration, or small dot at the corner of the screen as an indicator of car mode so that there is less interrupting to the user who is driving. For example, the programming could instruct speaker 526 to make an alert sound, vibrator 528 to vibrate, and/or screen 508 to display a small dot.

In another embodiment, the apparatus could automatically establish a wireless communications link with a device in the car when car mode is initiated. For example, the programming would instruct the wireless communications transceiver 202 to pair with a communications device in the car (e.g., over a Bluetooth connection). In this embodiment, the car may implement the similar circuit configuration as shown in FIG. 2 and FIG. 6. Hereinafter, it is assumed that the car has the same circuit configuration in those figures, and particularly FIG. 6. For purposes of this discussion, we will refer to the device in the vehicle corresponding to the configuration of FIG. 2 and FIG. 6 with the same reference numbers but with the suffix "c" appended thereto (e.g., screen 508c). In the car, screen 508c may be a heads-up display shown on the windshield or may be a screen implemented in a panel, and following discussion will assume that screen 508c is a heads-up display; namely, that the windshield in the car has a small area (heads-up display) comprising an OLED-type display that is transparent when no information is shown but that is capable of show information on that area.

Once the communication is set up in a car mode, the programming in the apparatus associated with processor 200 sends all of the information to be displayed on the screen 508 to the screen 508c in the car. In the car, a wireless communications circuit 202 would receive that information and, under the control of processor 200c, such information would be sent via a bus to screen 508c. In this embodiment, no information would be shown on the screen 508 of the apparatus, but would be displayed only on the screen 508c in the car to reduce distractions to the driver. As mentioned previously, the communications link between the apparatus and the car could be automatic or manual. When automatic, the information would be directed to display 508c without the need for user interaction.

In one embodiment of the car mode, one or more cameras in the apparatus would monitor whether, and how often, the user blinks his or her eyes. The programming in the apparatus, or programming downloaded from a server, would be configured to recognize whether the user is falling asleep based on how often the user blinks or how much user's pupils are moving. By using the recognized status of the user (e.g., how sleepy the user is), the programming in the apparatus would instruct vibrator 528 to shake strongly to wake up the user. In another embodiment, the programming would instruct screen 508 to flash strongly to alert the user. In a further embodiment, the programming would instruct speaker 526 to emit a loud sound to wake up the user. Flash pattern information, loud sound information and/or vibration patterns may be stored in memory 206 and accessed by processor 200 or retrieved from a remote server.

6. Translation Services Example

In another embodiment, the microphone 510 (FIG. 5) in the head worn apparatus would hear speech in a language. By, for example, using least location based information and the user's social graph data in addition to the sound heard and perhaps speech recognition technology, the apparatus would determine the most likely language and dialect being spoken. If the user's apparatus knows that the user does not understand the language being spoken due to, for example, the user's profile, the apparatus could communicate with the cloud/server to send and retrieve information in order to translate the speech and present the translated version to the user. This process would be performed automatically and the user would not need to manually input which language is being spoken, which dialect is being used, or which language into which to translate the speech.

7. Gameplay Example

In another embodiment, a user may wear the apparatus to play games with other people. For example, a user may receive Presentation Information about another person through the apparatus such as social graph settings and interests. The other person's interests may include playing a game such as a shoot up war game with plastic guns or a cops and robbers game. It is possible that each player has a head worn apparatus as described herein as well, so each player receives Presentation Data and other game data about the other players based on the screen and/or through the speaker. Each player may have a gun or a sword or a bow and arrow made up of a mold of plastic or some other material which connects to a user's device such as a smart phone. The smart phone and the head worn apparatus could be connected wirelessly or in a wired manner in order to communicate information about what is in the user's visual field through the apparatus and the smart phone or other user device sends information back to the apparatus about the user's movements with the molded device. Status reports of the game's progress between the two or more players is uploaded to the cloud/social graph network for further analysis on the server/cloud side. The social graph may help strangers or friends team up for game play through server side analytics.

8. Doctor and Patient Examples

In another embodiment, a doctor (DR) may want to stay connected with a patient group (PG) through a health-related social media channel. The patient group (PG) may comprise one or more patients P, the patient's family (PF), the patient's other doctors (PODs), the lab facilities (LF) where the patient gets various testing done such as blood testing labs, MRI, CT scans, and pharmaceutical information such as medicine picked up from a pharmacy (PH). In other words, PG could comprise P alone, or P plus any combination of PF, POD, LF and PH.

Suppose that the doctor DR wants to receive real time updates about the patient's (P) conditions through a health-related social media channel. The social media channel could include just the doctor (DR) and the patient (P) or it could include a patient group (PG) of others who are designated by the patient in order to help with the patient's treatment.

The lab (LF) could also be a part of the patient group (PG) in order to provide lab results to the doctors (DR; POD) in the patient's social graph. A user device, such as described herein which has a display, may provide data to the doctors (DR; POD) concerning his/her patient (P) in an order that is determined by an algorithm based on the doctors' (DR; POD) preset conditions and/or the characteristics of the level of seriousness of the a patent's (P) conditions so that the doctors (DR; POD) may monitor the patient in a predefined order of importance. The display could be updated based on the seriousness of each of the patient's (P) conditions. Certain alarms could alert a doctor (DR; POD) if a patient's (P) condition worsens or the patient (P) is in a dire position.

One or more sensors may be in or on the patient's (P) body and/or surroundings. Such sensors may include capsules with video/still cameras that may be ingested by a human and/or animal; sensors that appear on contact lenses whereby such contact lenses contain a wireless chip that transmits information captured by the contact lens; eyeglass or other head worn sensors; sensors as described above that may determine, for example, a patient's body temperature; a smart wrist watch that determines the patient's blood pressure, heart rate, and movement; a finger sensor that determines the blood oxygen level of a patient; a smart phone or other device that may determine the patient's movement through, for example, GPS, video/still cameras in the patient's environment such as a video camera that captures whether a patient is moving around his/her home or taking pills on time. A timer device is another type of sensor. The information collected by these sensors is uploaded to the cloud/server through an access point in the home.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors, such as, for example, location, a timing event, detection of an object, detection of a facial expression, detection of location, detection of a change in location, or other factors. It will further be appreciated that as used herein, that the terms processor, central processing unit (CPU), and computer are used synonymously to denote a device capable of executing the programming and communication with input/output interfaces and/or peripheral devices.

From the discussion above it will be appreciated that the technology can be embodied in various ways, including but not limited to the following:

1. A social graph based information recommendation engine, comprising: (a) a processor; (b) programming stored in a non-transitory medium readable and executable by the processor, wherein the programming performs steps comprising: (i) receiving sensor input; (ii) retrieving information of interest to a user of the recommendation engine based on the sensor input and information associated with the user; and (iii) outputting the information of interest to the user.

2. A social graph based information recommendation engine, comprising: (a) a processor; (b) programming stored in a non-transitory medium readable and executable by the processor, wherein the programming performs steps comprising: (i) receiving sensor input; (ii) retrieving information of interest to a user of the recommendation engine based on the sensor input, information associated with the user, and information associated with a person who is not the user; and (iii) outputting the information of interest to the user.

3. The recommendation engine of any preceding embodiment: wherein the information associated with the user is stored in memory associated with the processor and the programming; or wherein the information associated with the user is stored on a server accessible by the processor and the programming.

4. The recommendation engine of any preceding embodiment, wherein the information associated with the user comprises a user profile.

5. The recommendation engine of any preceding embodiment, wherein the information associated with the user comprises user preference information.

6. The recommendation engine of any preceding embodiment, wherein the information associated with the person who is not the user is stored on a server.

7. The recommendation engine of any preceding embodiment, wherein the information associated with the person who is not the user comprises a profile associated with that person.

8. The recommendation engine of any preceding embodiment, wherein the sensor input comprises input from one or more sensors selected from the group consisting of a video sensor, an audio sensor, a location sensor, a heading sensor, a touch sensor, an accelerometer, a temperature sensor, a precipitation sensor, and a motion sensor.

9. The recommendation engine of any preceding embodiment, wherein the information of interest is outputted to one or more devices selected from the group consisting of a visual display device, an audio output device, a vibratory device, and a communications interface device.

10. The recommendation engine of any preceding embodiment, wherein the information of interest to the user is stored on one or more servers.

11. The recommendation engine of any preceding embodiment, wherein the one or more servers are selected from the group consisting of social media servers, content servers, news servers, data servers, encyclopedia servers, and servers hosting user profiles.

12. The recommendation engine of any preceding embodiment, wherein the one or more servers are selected from the group consisting of standalone servers, cluster servers, networked servers, and servers connected in an array.

13. The recommendation engine of any preceding embodiment, wherein retrieval of information of interest to the user is initiated by one or more actions selected from the group consisting of user initiation, a timing event, detection of an object, detection of a facial expression, detection of location, detection of a change in location.

14. The recommendation engine of any preceding embodiment, further comprising a communications interface accessible by the processor and programming.

15. The recommendation engine of any preceding embodiment, wherein the communications interface is selected from the group consisting of a wired communications interface, a wireless communications interface, a cellular communications interface, a WiFi communications interface, a near field communications interface, an infrared communications interface, and a Bluetooth communications interface.

16. The recommendation engine of any preceding embodiment, wherein the recommendation engine is a component of a wearable device.

17. The recommendation engine of any preceding embodiment, wherein said wearable device is selected from the group consisting of eyeglasses, goggles, hats, wristwatches, pendants, and necklaces.

18. The recommendation engine of any preceding embodiment, wherein the recommendation engine is a component of a smart device.

19. The recommendation engine of any preceding embodiment, wherein the smart device is selected from the group consisting of smartphones, video display devices, televisions, tablet computers, laptop computers, notebook computers, personal computers, Blu-ray players, DVD players, and set top boxes.

20. A social graph based information retrieval apparatus, comprising: one or more sensors; one or more output devices; one or more communications interfaces; a processor; programming stored in a non-transitory medium readable and executable by the processor, wherein the programming performs steps comprising: receiving input from the one or more sensors; retrieving information of interest to a user of the apparatus based on input from the one or more sensors and information associated with the user; and outputting the information of interest to the user on the one or more output devices.

21. A social graph based information retrieval apparatus, comprising: one or more sensors; one or more output devices; one or more communications interfaces; a processor; programming stored in a non-transitory medium readable and executable by the processor, wherein the programming performs steps comprising: receiving input from the one or more sensors; retrieving information of interest to a user of the apparatus based on input from the one or more sensors, information associated with the user, and information associated with a person who is not the user; and outputting the information of interest to the user on the one or more output devices.

22. The apparatus of any preceding embodiment: wherein the information associated with the user is stored in memory associated with the processor and the programming; or wherein the information associated with the user is stored on a server accessible by the processor and the programming.

23. The apparatus of any preceding embodiment, wherein the information associated with the user comprises a user profile.

24. The apparatus of any preceding embodiment, wherein the information associated with the user comprises user preference information.

25. The apparatus of any preceding embodiment, wherein the information associated with the person who is not the user is stored on a server.

26. The apparatus of any preceding embodiment, wherein the information associated with the person who is not the user comprises a profile associated with that person.

27. The apparatus of any preceding embodiment, wherein the one or more sensors are selected from the group consisting of a video sensor, an audio sensor, a location sensor, a heading sensor, a touch sensor, an accelerometer, a temperature sensor, a precipitation sensor, and a motion sensor.

28. The apparatus of any preceding embodiment, wherein the one or more output devices are selected from the group consisting of a visual display device, an audio output device, a vibratory device, and a communications interface device.

29. The apparatus of any preceding embodiment, wherein the information of interest to the user is stored on one or more servers.

30. The apparatus of any preceding embodiment, wherein the one or more servers are selected from the group consisting of social media servers, content servers, news servers, data servers, encyclopedia servers, and servers hosting user profiles.

31. The apparatus of any preceding embodiment, wherein the one or more servers are selected from the group consisting of standalone servers, cluster servers, networked servers, and servers connected in an array.

32. The apparatus of any preceding embodiment, wherein retrieval of information of interest to the user is initiated by one or more actions selected from the group consisting of user initiation, a timing event, detection of an object, detection of a facial expression, detection of location, detection of a change in location.

33. The apparatus of any preceding embodiment, wherein the communications interface is selected from the group consisting of a wired communications interface, a wireless communications interface, a cellular communications interface, a WiFi communications interface, a near field communications interface, an infrared communications interface, and a Bluetooth communications interface.

34. The apparatus of any preceding embodiment, wherein the apparatus comprises a wearable device.

35. The apparatus of any preceding embodiment, wherein said wearable device is selected from the group consisting of eyeglasses, goggles, hats, wristwatches, pendants, and necklaces.

36. The apparatus of any preceding embodiment, wherein the apparatus comprises a smart device.

37. The apparatus of any preceding embodiment, wherein the smart device is selected from the group consisting of smartphones, video display devices, televisions, tablet computers, laptop computers, notebook computers, personal computers, Blu-ray players, DVD players, and set top boxes.

38. A social graph based information retrieval system, comprising: (a) one or more servers; (b) a user device, said user device comprising: (i) one or more sensors; (ii) one or more output devices; (iii) one or more communications interfaces; (iv) a processor; (v) programming stored in a non-transitory medium readable and executable by the processor, wherein the programming performs steps comprising: receiving input from the one or more sensors; retrieving information of interest to a user of the user device based on input from the one or more sensors and information associated with the user; and outputting the information of interest to the user on the one or more output devices.

39. A social graph based information retrieval system, comprising: (a) one or more servers; (b) a user device, said user device comprising: (i) one or more sensors; (ii) one or more output devices; (iii) one or more communications interfaces; (iv) a processor; (v) programming stored in a non-transitory medium readable and executable by the processor, wherein the programming performs steps comprising: receiving input from the one or more sensors; retrieving information of interest to a user of the user device based on input from the one or more sensors, information associated with the user, and information associated with a person who is not the user; and outputting the information of interest to the user on the one or more output devices.

40. The system of any preceding embodiment: wherein the information associated with the user is stored in memory associated with the processor and the programming; or wherein the information associated with the user is stored on one or more of the servers and is accessible by the processor and the programming.

41. The system of any preceding embodiment, wherein the information associated with the user comprises a user profile.

42. The system of any preceding embodiment, wherein the information associated with the user comprises user preference information.

43. The system of any preceding embodiment, wherein the information associated with the person who is not the user is stored on a server.

44. The system of any preceding embodiment, wherein the information associated with the person who is not the user comprises a profile associated with that person.

45. The system of any preceding embodiment, wherein the one or more sensors are selected from the group consisting of a video sensor, an audio sensor, a location sensor, a heading sensor, a touch sensor, an accelerometer, a temperature sensor, a precipitation sensor, and a motion sensor.

46. The system of any preceding embodiment, wherein the one or more output devices are selected from the group consisting of a visual display device, an audio output device, a vibratory device, and a communications interface device.

47. The system of any preceding embodiment, wherein the information of interest to the user is stored on the one or more servers.

48. The system of any preceding embodiment, wherein the one or more servers are selected from the group consisting of social media servers, content servers, news servers, data servers, encyclopedia servers, and servers hosting user profiles.

49. The system of any preceding embodiment, wherein the one or more servers are selected from the group consisting of standalone servers, cluster servers, networked servers, and servers connected in an array.

50. The system of any preceding embodiment, wherein retrieval of information of interest to the user is initiated by one or more actions selected from the group consisting of user initiation, a timing event, detection of an object, detection of a facial expression, detection of location, detection of a change in location.

51. The system of any preceding embodiment, wherein the communications interface is selected from the group consisting of a wired communications interface, a wireless communications interface, a cellular communications interface, a WiFi communications interface, a near field communications interface, an infrared communications interface, and a Bluetooth communications interface.

52. The system of any preceding embodiment, wherein the user device comprises a wearable device.

53. The system of any preceding embodiment, wherein said wearable device is selected from the group consisting of eyeglasses, goggles, hats, wristwatches, pendants, and necklaces.

54. The system of any preceding embodiment, wherein the user device comprises a smart device.

55. The system of any preceding embodiment, wherein the smart device is selected from the group consisting of smartphones, video display devices, televisions, tablet computers, laptop computers, notebook computers, personal computers, Blu-ray players, DVD players, and set top boxes.

Although the description above contains many details, these should not be construed as limiting the scope of the technology but as merely providing illustrations of some of the presently preferred embodiments of this technology. Therefore, it will be appreciated that the scope of the present technology fully encompasses other embodiments which may become obvious to those skilled in the art, and that the scope of the present technology is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present technology, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A social graph based information recommendation engine apparatus, comprising:

a smart device of a user, said smart device having a
display screen, microphone, front-facing camera and
rear-facing camera;
a wireless communications interface configured for com-
municating with one or more content servers on a
network;
a processor within said smart device; and
programming stored in a non-transitory medium on said
smart device and readable and executable by the pro-
cessor, wherein the programming performs steps com-
prising:
tracking types of applications used by the user and the
amount of time spent on the applications;
receiving sensor input from at least said microphone,
front-facing camera, and rear-facing camera;
retrieving user preferences from user profile settings;
establishing a connection over said network through
social channels to the social network of the user;
retrieving information of interest to the user of the
recommendation engine over said wireless commu-
nications interface from one or more content servers
for the social channels, wherein content retrieved is
based on tracking types of applications and amount
of time spent on the application, as well as the sensor
input, information associated with the user including
said user preferences, and information associated
with a person on the social network who is not the
user; and
filtering said information of interest by utilizing ana-
lytical processing techniques to filter out information
that may not be interesting to the user;
sorting said information of interest by categories of
information having different priorities;
generating social graph based recommendations by
outputting social content information of interest to
the user on the display screen of the smart device,
with the existence of lower priority information
displayed on the display screen as one or more icons.

2. The recommendation engine of claim 1:
wherein the information associated with the user is stored
in memory associated with the processor and the pro-
gramming; or
wherein the information associated with the user is stored
on a server accessible by the processor and the pro-
gramming.

3. The recommendation engine of claim 1, wherein said
tracking further comprises tracking web sites/blogs used by
the user and the amount of time spent on these web sites/
blogs.

4. The recommendation engine of claim 1, wherein social
content information being output on the display screen of the
smart device is selected from the group of content consisting
of video, images, text and audio.

5. The recommendation engine of claim 1, wherein the
information associated with the person on the social network
who is not the user is stored on a server.

6. The recommendation engine of claim 1, wherein the
information associated with the person on the social network
who is not the user comprises a profile associated with that
person.

7. The recommendation engine of claim 1, wherein the
sensor input comprises input from one or more sensors
selected from the group consisting of a video sensor, an
audio sensor, a location sensor, a heading sensor, a touch
sensor, an accelerometer, a temperature sensor, a precipita-
tion sensor, and a motion sensor.

8. The recommendation engine of claim 1, wherein the
information of interest is outputted to one or more devices
selected from the group consisting of a visual display device,
an audio output device, a vibratory device, and a commu-
nications interface device.

9. The recommendation engine of claim 1, wherein the
information of interest to the user is stored on one or more
servers.

10. The recommendation engine of claim 9, wherein the
one or more servers are selected from the group consisting
of social media servers, content servers, news servers, data
servers, encyclopedia servers, and servers hosting user pro-
files.

11. The recommendation engine of claim 1, wherein
retrieval of information of interest to the user is initiated by
one or more actions selected from the group consisting of
user initiation, a timing event, detection of an object, detec-
tion of a facial expression, detection of location, and detec-
tion of a change in location.

12. The recommendation engine of claim 1, further com-
prising a communications interface accessible by the pro-
cessor and programming.

13. The recommendation engine of claim 1, wherein the
recommendation engine is a component of a wearable
device.

14. The recommendation engine of claim 13, wherein said
wearable device is selected from the group consisting of
eyeglasses, goggles, hats, wristwatches, pendants, and neck-
laces.

15. The recommendation engine of claim 1, wherein the
recommendation engine is a component of a smart device.

16. The recommendation engine of claim 15, wherein the
smart device is selected from the group consisting of smart-
phones, video display devices, televisions, tablet computers,
laptop computers, notebook computers, personal computers,
Blu-ray players, DVD players, and set top boxes.

17. A social graph based information retrieval apparatus,
comprising:
a smart device of a user, said smart device having a
display screen, and multiple sensors including a micro-
phone, front-facing camera and rear-facing camera;
a wireless communications interface configured for com-
municating with one or more content servers on a
network;
a processor within said smart device; and
programming stored in a non-transitory medium readable
and executable by the processor, wherein the program-
ming performs steps comprising:
tracking web sites/blogs and types of applications used
by the user, and the amount of time spent on the web
sites/blogs and applications;
receiving sensor input from at least said microphone,
front-facing camera, and rear-facing camera;
retrieving user preferences from user profile settings;
establishing a connection over said network through
social channels to the social network of the user;
retrieving information of interest to user of the appa-
ratus over said wireless communications interface
from one or more content servers for the social
channels, wherein content retrieved is based on
tracking types of applications and amount of time per
application as well as sensor input and information
associated with the user including said user prefer-
ences, and information associated with a person on
the social network who is not the user;

filtering said information of interest by utilizing analytical processing techniques to filter out information that may not be interesting to the user;

sorting said information of interest by categories of information having different priorities; and generating social graph based recommendations by outputting social content information of interest to the user on the display screen of the smart device, with the existence of lower priority information displayed on the display screen as one or more icons.

18. The apparatus of claim 17:

wherein the information associated with the user is stored in memory associated with the processor and the programming; or wherein the information associated with the user is stored on a server accessible by the processor and the programming.

19. The apparatus of claim 17, wherein social content information being output on the display screen of the smart device is selected from the group of content consisting of video, images, text and audio.

20. The apparatus of claim 17, wherein retrieval of information of interest to the user is initiated by one or more actions selected from the group consisting of user initiation, a timing event, detection of an object, detection of a facial expression, detection of location, and detection of a change in location.

21. The apparatus of claim 17, wherein the apparatus comprises a wearable device.

22. The apparatus of claim 21, wherein said wearable device is selected from the group consisting of eyeglasses, goggles, hats, wristwatches, pendants, and necklaces.

23. The apparatus of claim 17, wherein the apparatus comprises a smart device.

24. The apparatus of claim 23, wherein the smart device is selected from the group consisting of smartphones, video display devices, televisions, tablet computers, laptop computers, notebook computers, personal computers, Blu-ray players, DVD players, and set top boxes.

* * * * *